US012806124B2

(12) United States Patent
Dang Thi et al.

(10) Patent No.: US 12,806,124 B2
(45) Date of Patent: Nov. 24, 2026

(54) PROCESS FOR PRODUCING A COMPOUND FOR LIPID TREATMENT OF DAMAGED HAIR USING LIPID MOLECULE MIXTURE

(71) Applicant: Moonshot Biotech PTE.LTD, Singapore (SG)

(72) Inventors: Hong Ngoc Dang Thi, Ho Chi Minh city (VN); Nam Hai Lai, Ho Chi Minh city (VN)

(73) Assignee: MOONSHOT BIOTECH PTE. LTD, Singapore (SG)

( * ) Notice: Subject to any disclaimer, the term of this patent is extended or adjusted under 35 U.S.C. 154(b) by 219 days.

(21) Appl. No.: 18/907,657

(22) Filed: Oct. 7, 2024

(65) Prior Publication Data

US 2025/0195344 A1 Jun. 19, 2025

(30) Foreign Application Priority Data

Dec. 19, 2023 (VN) .............................. 1-2023-09048

(51) Int. Cl.
*A61K 8/04* (2006.01)
*A61Q 5/00* (2006.01)

(52) U.S. Cl.
CPC ................ *A61K 8/04* (2013.01); *A61Q 5/002* (2013.01); *A61K 2800/21* (2013.01); *A61K 2800/413* (2013.01); *A61K 2800/5922* (2013.01); *A61K 2800/805* (2013.01)

(58) Field of Classification Search
None
See application file for complete search history.

(56) References Cited

U.S. PATENT DOCUMENTS

2020/0346174 A1* 11/2020 Dang ..................... A23D 7/011
2021/0277325 A1* 9/2021 Dang ..................... A61Q 19/00

* cited by examiner

*Primary Examiner* — Danah Al-Awadi
(74) *Attorney, Agent, or Firm* — United One Law Group LLC; Kongsik Kim; Jhongwoo Peck

(57) ABSTRACT

A process for producing a compound for lipid treatment of hair using lipid molecule mixture includes (a) preparing a mixture with lipid molecular structure by preparing a molecule mixture, comprising argan oil, olive oil, and camellia oil, heating the mixture to a temperature between 60 and 100° C.; preparing a carrier by heating propylene glycol monocaprylate and lecithin; adding the carrier to a dispersed phase; adding polysorbate 80 and polysorbate 60 to the mixture of the carrier and the dispersed phase; cooling and homogenizing the solution by an ultrasonic homogenizer, and emulsifying in an emulsification device; and (b) introducing the lipid molecule mixture from the vegetable oils into chemical ingredients to produce a compound for lipid treatment of hair.

5 Claims, 5 Drawing Sheets

Before use After use

Before use After use

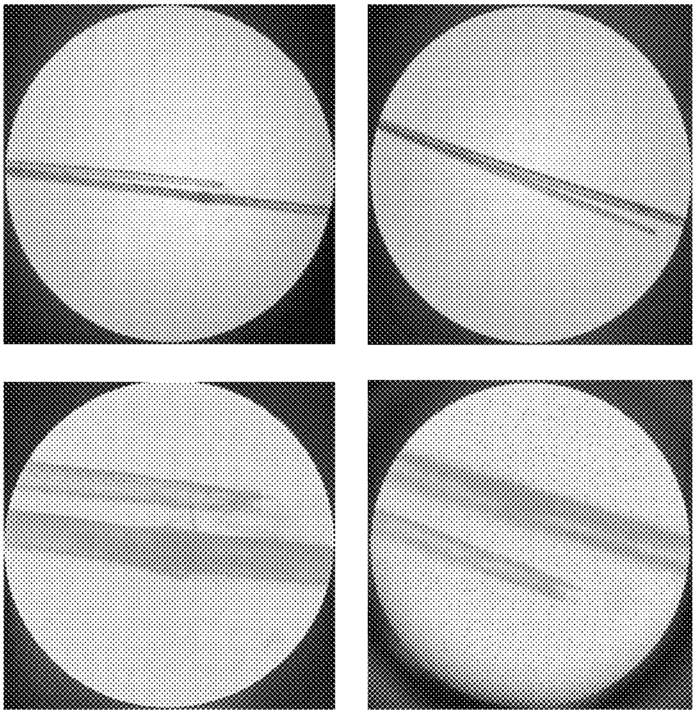
*Hair before use* *Hair after a single use*
FIG. 4A FIG. 4B

PROCESS FOR PRODUCING A COMPOUND FOR LIPID TREATMENT OF DAMAGED HAIR USING LIPID MOLECULE MIXTURE

CROSS-REFERENCE TO RELATED APPLICATION

This application claims priority from Vietnamese Application No. 1-2023-09048 filed Dec. 19, 2023, which is incorporated herein by reference in its entirety.

TECHNICAL FIELD

The present invention relates to the field of cosmetic chemistry for hair and scalp care, in particular, to a process for producing a compound for treatment of lipid loss in hair, which is damaged by heat, styling chemicals, and dyeing, whereby the lipid bonds in the hair are broken and lost, causing hair damage, with mixture of lipid molecules contained in a mixture of 3 types of oils, comprising argan oil, olive oil, and camellia oil.

RELATED ART

Hair comprises a variety of lipids, carbohydrates, and proteins that are the structural foundation of hair. Lipids only account for 2 to 6% of hair, but are essential to create healthy hair.

Inside hair, lipids function as cement and other components as the building structural blocks for hair. This means that lipids bind the structural blocks together to make up hair. Lipid loss will lead to loss of connectivity, protein, and other agents, resulting in reduced hair elasticity and making hair weak and prone to breakage.

On the surface of a hair strand, cells are covered with a lipid layer which is covalently bound to the proteins of the hair strand that protect the hair structure, keeping the hair moist, shiny, soft, and smooth. Integral hair lipids (IHL) is bound to the keratinized cell surface to form make an environmentally resistant lipid envelope. It is mainly located on the hair cuticle and the inner root sheath. The main components of IHL are fatty acids, phytosphingosine, and ceramides in descending order. Other components of IHL are cholesterols, cholesterol sulfates, and cholesterol oleates (the lipid acid content will depend on the hair position, for example, hair follicles, hair shafts, hair roots). The cuticle cell surface or cell surface in hair is rich in fatty acids, unlike the keratinized areas of the cuticle or sebaceous glands, and about 30-40% of such fatty acids comprise 18-methyl-eicosanoic acid which is known to be bound to proteins by ester or thioester bond.

During hair treatment, such as coloring, hair dyes open the cuticle to increase the absorption of coloring agents into the hair. This mechanism seriously damages the protective lipid layer, reduces softness and brightness, and causes static electricity to become difficult to comb and dry. Damage to the lipid layer also leads to loss of protein and broken bonds in the hair, especially the lipid bonds. In addition, our hair is daily exposed to various harmful external influences, such as sunlight, pollution, and shampoo detergents, etc., which damage the hair lipid layer, causing daily lipid loss. In particular, without the protection of the lipid layer, the ultraviolet rays of sunlight may damage hair, causing fiber deterioration. UV-B rays attack pigments and protein fractions in hair, and UV-A rays induce reactive oxygen species (ROS) through the interaction of endogenous photosensitizers.

Lipids in hair cannot be supplemented normally because each position in the hair will have a different lipid content, specifically, the lipid content of human hair is different from that of the cuticle (TABLE 1).

- In whole human hair follicle, it is composed of fatty acid, phytosphingosine, ceramide, cholesterol, and cholesterol sulfate in descending order.
- In IRS (inner root sheath), hair lipid is composed of fatty acid, phytosphingosine, ceramide, cholesterol, and cholesterol oleate in descending order.
- In hair shaft, it is composed of phytosphingosine, fatty acid, ceramide, cholesterol, and cholesterol sulfate in descending order, which is different from the lipid composition in the cuticle.

TABLE 1

Lipid composition in hair

| | Sebum (%) | Epidermis (%) | Hair shaft (mg/g) | IRS (inner root sheath) (mg/g) | Follicle (%) |
|---|---|---|---|---|---|
| Free cholesterol | 5 | 26.0 ± 0.6 | 0.5 | 0.5 | 3.7 |
| Free fatty acid | — | 13.1 ± 1.6 | 4.0 | 23.4 | 29.6 |
| Cholesterol sulfate | — | 3.9 ± 1.4 | 2.9 | 0.4 | 0.3 |
| Triglyceride | 57 | — | — | 0.2 | — |
| Cholesteryl esters | 5 | 1.7 ± 1.1 | — | — | — |
| Glucosyl | — | 1.0 ± 0.6 | — | — | — |
| Unidentified | — | 5.7 ± 0.9 | — | — | — |
| Sphingosine | — | — | — | — | 26.3 |
| Wax ester | 26 | — | — | 4.1 | — |
| Squalene | 12 | — | — | <0.2 | — |

Therefore, the addition of lipids to hair is very important, but until now there has been no product that can do this optimally for hair because hair has a complex structure, which is impenetrable, and the properties of oil are not suitable for incorporation into the product.

In cosmetic chemistry, the use of vegetable oils in hair care is widely applied. Oils, such as argan oil, olive oil, camellia oil, etc., are all made up of lipids comprising fatty acid and triglyceride. All oils have the disadvantage of being insoluble in water and unstable during heat treatment and storage, making it very difficult to apply on an industrial production scale. In addition, the use of conventional oils is not very effective, which causes stickiness, and is almost impossible, even if put into the product, for the hair to absorb.

Therefore, it is essential to improve the stability, reduce the denaturation during production, improve the dispersibility in water, increase the permeability, and increase the bioavailability of oils. Application of nanotechnology is a new technological approach to form a delivery system and enhance the bioavailability of agents. With a small particle size, which can be adjusted according to product needs, the stability, absorption, and retention of oil in the product will be increased. Nanoemulsion can be used as a delivery system to increase stability. There is a need for a process to produce a microemulsion system of microparticles of less than 100 nm that is uniform and has better water solubility while retaining its structure and activity. Nanoemulsion is favorable for absorption in the intestine, which is easily dispersed in liquid medium. A nanoemulsion with lipid molecule mixture helps to increase absorption, especially used in some foods for people who have problems swallowing solid dosage forms. Encapsulation in nanoparticles and formulation as an O/W system (which is an oil/aqueous system, with droplets dispersed in water) minimizes the fishy odor and undesirable taste of some oil triglycerides.

Dang, H. N. T, & Lai, N. H., 2020 provided a process for producing a nano-microemulsion system of plant oil triglycerides in US20200346174A1, titled "Process for producing a nano-microemulsion system of plant oil triglycerides." The process for producing a microemulsion system of triglycerides allows the formation of uniform miniscule droplets, which are soluble and stable in water for a long term without changes in activity or structure, increasing the efficiency of oil use, specifically increasing the absorption and bioavailability applicable on an industrial scale.

Sirikarn Pengona et al in a study on "The effect of surfactant on the physical properties of coconut oil nanoemulsions," 2018, researched and developed a form of coconut oil compatible with water through nano emulsification. The results show that coconut oil nanoparticles using polyethylene glycol octyl phenyl ether (PGO) and polyoxyethylene sorbitan monostearate (POS) as surfactants presented a low creaming index, which indicates excellent stability, while those containing sodium lauryl sulfate (SLS) and poloxamer 407 (PLX) presented a higher creaming index, which indicates lower physical stability. The droplet size of the nanoparticles decreased from 33 μm to less than 200 nm with an increase in the amount of PHC from 1% to 10% by weight. However, in this study, the particle size was more than 200 nm and the particles were not uniform and the oil ratio in the system was only 5%, making it unstable in water.

Hiren C. et al in a study on "Formulation and evaluation of o/w nanoemulsion of ketoconazole," 2013, provided nanoparticles with a size of 100 nm to 1000 nm in an optimized formulation to produce an oil-in-water microemulsion system for in vivo laboratory research to increase the bioavailability of oils. However, the formulation is only applied on the experimental scale and the particle size is larger than 100 nm and is not uniform, making it difficult to apply on the industrial scale.

Klein et al. in the of International Patent Publication No. WO 2017/059513 A2 titled "Nanoemulsion compositions and methods" provided microemulsion particles with a size of 100 nm to 300 nm and particles of less than 100 nm. This is a process of an oil-water emulsion system for use in cosmetic products using surfactants. In addition, in this process Massocare™ HCO 40 (hydrogenated castor oil PEG-40), Lipocol™ HCO 60 (hydrogenated castor oil PEG-60), Myrj™ S20, S50, or S100 (PEG-20, -50, or -100 stearate), and/or PEG-3 oleate were used. This group of PEGs, while approved for use, is produced through a process called ethoxylation, a chemical reaction wherein ethylene oxide is added to the substrate. The PEG formation process involves ethylene oxide and 1,4-dioxane, which is a potentially dangerous byproduct. For this reason, PEG is not approved in certified organic cosmetics in Europe and there are currently mixed opinions about the side effects when used long-term, and some types of PEG below 100 have been restricted from use in products.

The study "Follicular delivery of spironolactone via nanostructured lipid carriers for management of alopecia" by Shamma, R. N., and Aburahma, M. H. (2014) provided a nanostructured olive carrier with a size of 215.6 to 834.3 nm, by differential scanning calorimetry and X-ray diffraction, showing that a massive release of active ingredients in the early stage, followed by sustained release, delivered the active ingredients to the scalp hair follicles.

The study "Composition for caring for keratin materials" by Amit Jayaswal, Cherry Yang, Shichen Zhang (2019) provided an oil-in-water (O/W) emulsion composition that is useful in products for conditioning keratin materials, comprising: a fatty acid-ester mixture; and at least one cationic surfactant. The composition for conditioning keratin materials comprises: an oil phase including a fatty acid-ester mixture (A) comprising: a fatty acid composition (A-I) comprising a plurality of, for example, at least 3, 4, or 5 medium-chain fatty acids, and an ester composition (A-II) comprising a plurality of, for example, at least 3, 4, or 5 single esters of medium-chain fatty acids; wherein a medium chain fatty acid means a monocarboxylic acid having between 6 and 20 carbon atoms; and at least one cationic surfactant (B). The study aimed to produce a composition to support the delivery of keratin to hair and hair follicles.

In the study "Oil compositions" by Jonathan Edelson, Timothy KotylaKlaus, Theobald (2012) provided an oil composition, related methods and reagents, which are especially useful for the treatment of dermatological conditions. In some embodiments, the provided composition is formulated to achieve dermal delivery, for example, by topical application, comprising an oil and an active ingredient intended for skin support, for example, the active ingredient also comprises one or more additional active ingredients for treatment of acne, unwanted sweating, hyperhidrosis, body odor, sweating disorder, pigmentation disorder, rosacea, alopecia, psoriasis, actinic keratosis, eczematous dermatitis, excess sebum production disorder, burn, Raynaud's phenomenon, lupus erythematosus, hyperpigmentation disorder, hypopigmentation disorder, skin cancer, skin infection, facial wrinkle, and/or a combination thereof, and an oil agent selected from a group comprising soybean oil, coconut oil, canola oil, safflower oil, olive oil, corn oil, cottonseed oil, flaxseed oil, palm oil, peanut oil, sunflower oil, rice bran oil, sesame oil, cocoa butter, almond oil, cashew oil, hazelnut oil, macadamia oil, mongongo seed oil, pecan oil, pine nut oil, pistachio oil, sachainchi oil, walnut oil, gourd oil, buffalo gourd oil, pumpkin oil, pumpkin seed oil, watermelon seed oil, acai oil, blackcurrant seed oil, borage seed oil, evening primrose oil, carob pod oil, amaranth oil, apricot oil, apricot kernel oil, apple seed oil, argan oil, artichoke oil, avocado oil, babassu oil, ben oil, Borneo shea oil, chestnut oil, cinnamon oil, cocoa butter, oyster oil, cohune oil, coriander seed oil, dika oil, grapeseed oil, hemp oil, oil cottonseed, kenaf seed oil, lallemantia oil, marula oil, meadowfoam seed oil, mustard oil, nutmeg butter, okra seed oil, papaya seed oil, perilla seed oil, pequi oil, poppy seed oil, plum seed oil, quinoa oil, ramtil oil, royle oil, tea seed oil, thistle oil, tigernut oil, tomato seed oil, wheat germ oil, radish oil, salicornia oil, tung oil, algae oil, copaiba oil, honge oil, jatropha oil, petroleum seed oil, silicone oil, mineral oil, lauroyl macrogol-6 glyceride, lauroyl polyoxyl-6 glyceride, oleoyl macrogol-6 glyceride, oleoyl polyoxyl-6 glyceride, linoleoyl macrogol-6 glyceride, linoleoyl polyoxyl-6 glyceride, propylene glycol monocaprylate, propylene glycol monolaurate, propylene glycol monolaurate, polglyceryl-3 dioleate, propylene glycol dicaprylocaprate, diethyl glycol monethyl ether, caprylocaproyl macrogol-8 glyceride, caprylocaproyl polyoxyl-8 glyceride, bergamot, cade, chamomile, caraway, carnauba, castor, cinnamon, cod liver, coffee, emu, eucalyptus, fish, geraniol, hyssop, jojoba, kukui seed, lavandin, lavender, lemon, *Litsea cubeba*, mallow, mango seed, mink, orange, rough orange, palm kernel, peach kernel, rosemary, sandalwood, sasquana, salty, sea buckthorn, shea butter, tea, tsubaki, vetiver, butyl stearate, caprylic triglyceride, capric triglyceride, cyclomethicone, diethyl sebacate, dimethicone 360, isopropyl myristate, octyldodecanol, oleyl alcohol, and mixtures thereof. In this study, a combined composition of oil and therapeutic agents without microemulsification was provided.

The study "Silk hair care compositions" by Sara A. Johnson, Carlos J. Bosques Gregory H. et al. (2020) described a silky hair care composition as well as a method of using and producing the same. In this study, the inventors used proteins with peptides of different fragments, comprising a fiber fragment with an average molecular weight selected from the ranges of about 1 kDa to about 5 kDa, about 5 kDa to about 10 kDa, about 6 kDa to about 17 kDa, about 10 kDa to about 15 kDa, about 10 kDa to about 15 kDa, about 15 kDa to about 20 kDa, about 17 kDa to about 39 kDa, about 20 kDa to about 25 kDa, about 25 kDa to about 30 kDa, about 30 kDa to about 35 kDa, about 35 kDa to about 40 kDa, about 39 kDa to about 80 kDa, about 40 kDa to about 45 kDa, about 45 kDa to about 50 kDa, about 60 kDa to about 100 kDa, and about 80 kDa to about 144 kDa, and polydispersity of 1 to about 5; lithium bromide of 0 to 500 ppm; sodium carbonate of 0 to 500 ppm; and a dermatologically approved carrier. In this study, the direction of protein supplementation in hair care was provided.

The above processes mainly produced coarse microparticles, so the dispersion efficiency in water is not high, the stability time is short, and conditions cannot be met if added to actual products. The studies in experimental models, the employment of tools, equipment, and complex steps are difficult to apply on an industrial scale and cannot be adjusted to produce a desired particle size for each product line. In particular, the delivered oil content in the system is low, which is less than 20% and PEG used, so it does not meet the use demands.

In addition, due to the complexity of penetration into hair follicle, the three most common strategies that have been applied and proven through various studies, are shown in FIGS. 5A to 5C.

FIG. 5A illustrates the case where nanotechnology-based particles are used to deliver therapeutic agents into hair follicles. FIG. 5B illustrates the case where nanoparticles are used to deliver therapeutic agents directly to sites surrounding hair follicles. FIG. 5C illustrates the case where external stimuli lead to active release of the drug from particles with a specific release mechanism.

Particle size plays an important role in the penetration of the encapsulated active ingredients. Smaller particles appear to enhance penetration to a greater extent than larger particles. However, this conclusion is contradictory because it has proved that for the same type of nanoemulsion, there is no influence of emulsion droplet size on the ability of the encapsulated substance to penetrate through hair and skin when used in cosmetic chemistry. Compared to nanocapsule, nanoemulsion is more likely to penetrate and/or penetrate into hair and skin, possibly due to its flexibility and lack of polymers having affinity for the stratum corneum.

The study "Follicular delivery of spironolactone via nanostructured lipid carriers for management of alopecia" by Shamma, R. N., and Aburahma, M. H. (2014) used nanostructured olive carriers with a size range of 215.6 to 834.3 nm, by differential scanning calorimetry and X-ray diffraction, showing that a massive release of active ingredients in the early stage, followed by sustained release, delivered the active ingredients deep into the scalp hair follicles.

The study "Influence of the Vehicle on the Penetration of Particles into Hair Follicles" by Alexa Patzelt (2011) et al. found that the optimal size for penetration into hair follicles is between 400 and 700 nm, each size capable of selectively targeting different structures within hair follicles. Particles with a size of 470 nm are said to have the deepest penetration into the bulge in the hair follicle.

Rui Su et al. (2017) in the publication "Size-dependent penetration of nanoemulsions into cuticle and hair follicles: implications for transdermal delivery and immunization" tested nanoemulsions with three sizes (80-200-500 nm) to prove their penetration into intact hair follicles. The results indicated that the nanoemulsions were absorbed by antigen-presenting cells residing in the keratinocytes and perifollicular sites. It was finally concluded that the nanoemulsion with a particle size of 80 nm could penetrate possible cuticle as well as filling the whole hair follicle, while the nanoemulsion with a particle size of 500 nm could not effectively penetrate into the cuticle and only moved along the hair follicle, and finally the nanoemulsion with a particle size of 200 nm showed a moderate cross-axis delivery effect among the nanoemulsions of three sizes.

Therefore, the demand for raw materials to provide lipids for hair and for applications in cosmetic chemicals, and hair and skin care products is huge.

In US Patent Publication No. US20200346174A1, the inventors provided a "Process for production of nano-microemulsion system of plant oil triglycerides." With this process, the inventors produced a micro-nano emulsion system that is soluble and stable in water for a long term without changes in activity and structure, increasing the effectiveness of the active oil triglyceride, specifically increasing the absorption and bioavailability applicable on an industrial scale, is safe, and has particle stability over a long time, better dispersibility in water, and stability in aqueous systems for a long term while retaining the stable structure of lipids and triglycerides of vegetable oil. However, this patent did not provide a formulation for applying materials that provide lipids for hair and for application in cosmetic chemicals, hair and skin care products.

SUMMARY

The object of the invention is to provide a process for producing a compound for lipid treatment of hair using an oil mixture. The invention provides lipid particles that are biocompatible with hair lipids with an appropriate size for intended uses and with each hair and scalp area, capable of dissolving and being long-term stable in water while retaining stable activity and structure, thereby increasing the effectiveness of the active oil triglyceride, specifically increasing absorption and bioavailability. The particles can be applied on an industrial scale, are safe, and have long particle stability, better dispersibility in water, and long-term stability in aqueous systems, while retaining the stable structure of lipids and triglycerides of vegetable oil, especially forming a build lipid layer and lipid bonds to help improve lipid damage in hair. A hair treatment formulation comprises lipids as active agents for replenishing lost lipids from deep within the hair, rebuilding lipid bonds in the hair and scalp, which effectively nourishes and softens hair immediately after a single treatment, reduces breakage and produce anti-oxidation effects, reduces ROS for hair, replacing silicone in cosmetic chemicals. The compound helps repair the chemical, mechanical, and environmental damage to all hair types and textures, further restoring each hair strand for hours, after treatment.

The compound for lipid treatment of hair with lipid molecule mixture having a build lipid layer and lipid bonds that form lipid complexes that simulate the biolipid composition of hair, i.e., they mimic the components found in the lipid of undamaged and untreated hair. This restores fat lost due to time or color or chemical treatment, thereby restoring hair health, allowing for regeneration and repair from deep within the hair. Unlike old technologies that make it feel fake on the skin and hair, rely on softening and smoothing agents which form an outer membrane, but do not address the actual damage to the skin and hair such as silicone-dimethicone, dimethiconol, and these agents are non-biodegradable, which affects the environment, the vegetable oil nano system completely replaces silicone, and is safe and environmentally friendly. The invention aims to replace silicone and directly addresses the damages, restore and regenerate the damaged so that the skin and hair are soft, smooth, and healthy.

To achieve the above object, the invention provides a process for producing a compound for lipid treatment of hair with lipid molecule mixture, comprising:

(a) preparing a mixture with lipid molecular structure from vegetable oils by:

(i) preparing a dispersed phase of lipid molecule mixture by mixing 20 to 80 wt % of argan oil based on total oil weight, 10 to 60 wt % of olive oil based on total oil weight, and 10 to 20 wt % of camellia oil based on total oil weight, heating the mixture to a temperature between 60 and 100° C.;

(ii) preparing a carrier by heating propylene glycol monocaprylate (Capryol 90) and lecithin at a propylene glycol monocaprylate:lecithin weight ratio of 5:1 to a temperature between 60 and 100° C. under vacuum rotary evaporation, followed by cooling to about 30° C., ultrasonication for about 30 minutes, then magnetic stirring and heating at 60 to 100° C. for about 30 minutes, and then collecting the solution into the rotary evaporation system under stirring at 100° C.;

(iii) adding the carrier to the dispersed phase at a carrier: dispersed phase weight ratio of 3:1 while maintaining the temperature of the carrier and dispersed phase mixture between 60 and 100° C. under stirring at 400 to 800 rpm under vacuum; then spray shooting the whole solution through a system of high pressure homogenizer with integrated dispersion nozzle;

(iv) adding polysorbate 80 and polysorbate 60 to the carrier and dispersed phase mixture obtained in step (iii) at a polysorbate 80:polysorbate 60:carrier and dispersed phase mixture weight ratio of 3:1:1 while maintaining the temperature of the carrier and dispersed phase mixture between 60 and 100° C. under stirring at 400 to 800 rpm under vacuum;

(v) cooling the resulting mixed solution to about 25° C., homogenizing the solution using an ultrasonic homogenizer, performing ultrasonication for 30 to 60 minutes to achieve a size of less than 100 nm, the quality of the resulting product controlled by dissolution in water and transparency measurement, wherein if transparency is not met, the heating and transparency measurement is continued every 30 minutes until it is transparent, then the reaction is stopped, followed by emulsification in an emulsifying device under stirring at 400 to 800 rpm;

(b) introducing the mixture with lipid molecular structure from vegetable oils prepared above into chemical ingredients, by:

(i) preparing ingredients, by weight, as follows:

the mixture with lipid molecular structure obtained in step (a): 3-5%,
disodium EDTA: 0.1%,
Sodium C14-16 Olefin Sulfonate: 5-7%,
glycerin: 2-5%,
decyl glucoside: 1-5%,
PEG-7 glyceryl cocoate: 0.5-1%,
disodium laureth sulfosuccinate: 3-6%,
cocamidopropyl betaine: 3-5%,
polyquaternium-73:0.2-0.4%,
phenoxyethanol and ethylhexylglycerin: 0.8%,
25% citric acid solution: 0.2-1%,
water: to 100%;

(ii) preparing a compound for treatment of lipid loss in damaged hair, by:

dissolving disodium EDTA in water in a stirring bath;

heating under stirring at about 20 rpm at about 75° C.;

adding dissolved Sodium C14-16 Olefin Sulfonate to the stirring bath under stirring for about 40 minutes at about 20 rpm, at about 75° C.;

adding decyl glucoside to the stirring bath under stirring at about 25 rpm at about 75° C., with the stirring duration of about 10 minutes;

cooling the above-prepared solution to a temperature between 30 and 32° C. for about 60 minutes; during cooling to lower temperature, adding glycerin and PEG-7 glyceryl cocoate;

adding the mixture with lipid molecular structure to the stirring bath and stirring at about 25 rpm, stopping the heating, with the stirring duration of about 60 minutes;

adding disodium laureth sulfosuccinate to the stirring bath under stirring at about 25 rpm, stopping the heating, with the stirring duration of about 10 minutes;

adding polyquaternium-73 to the stirring bath under stirring at about 25 rpm, stopping the heating, with the stirring duration of about 10 minutes;

adding cocamidopropyl betaine to the stirring bath under stirring at about 20 rpm, stopping the heating, with the stirring duration of about 10 minutes;

adding phenoxyethanol, ethylhexylglycerin, and 25% citric acid solution to the stirring bath under stirring at about 20 rpm, stopping the heating, with the stirring duration of about 20 minutes;

checking the homogeneity of the solution via observation thereof and centrifugation at 3000 rpm for 30 minutes, wherein if the solution is not separated into layers and remains homogeneous, a compound for treatment of lipid loss in damaged hair will be obtained.

According to one aspect of the invention, in stage (i) of step (a) of the process for producing a compound for lipid treatment of hair using lipid molecule mixture, the argan oil:olive oil:camellia oil weight ratio is 2:6:2.

According to another aspect of the invention, in stage (i) of step (a) of the process for producing a compound for lipid treatment of hair using lipid molecule mixture, the argan oil:olive oil:camellia oil weight ratio is 4:4:2.

According to still another aspect of the invention, in stage (i) of step (a) of the process for producing a compound for lipid treatment of hair using lipid molecule mixture, the argan oil:olive oil:camellia oil weight ratio is 6:2:2.

According to yet another aspect of the invention, in stage (i) of step (a) of the process for producing a compound for lipid treatment of hair using lipid molecule mixture, the argan oil:olive oil:camellia oil weight ratio is 8:1:1.

BRIEF DESCRIPTION OF THE DRAWINGS

FIGS. 3A to 3D are images comparing the tested head halves of users, wherein FIGS. 3A and 3C are images of the upper half of the head before using the compound according to the invention, and FIGS. 3B and 3D are images of the upper half of the head after using the compound according to the invention.

FIGS. 4A and 4B are respective images observed, under an electron microscope, of the hair surface before using the compound according to the invention and after using the compound according to the invention.

DETAILED DESCRIPTION

Figure 1:
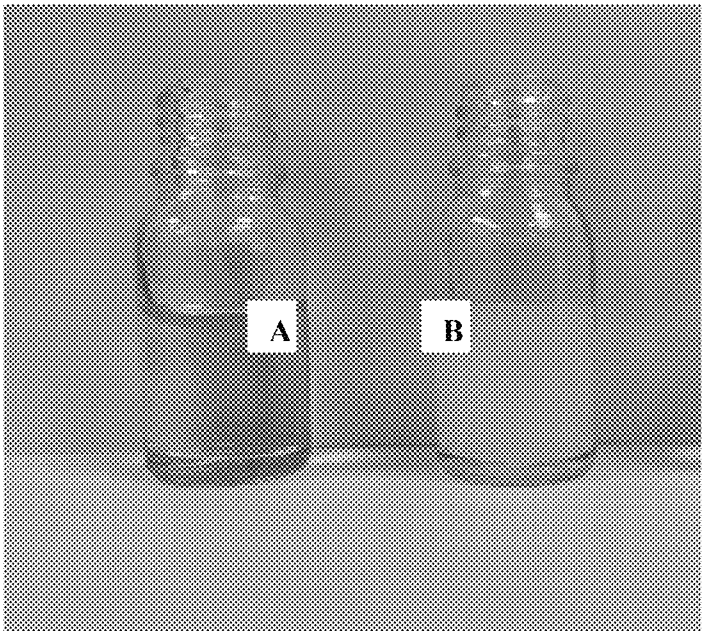
FIG. 1 is an image comparing the water dispersibility between a known lipid molecule mixture (A) and a lipid molecule mixture obtained by the process according to the invention (B).

A process for producing a compound for lipid treatment of hair using lipid molecule mixture according to the invention is carried out as follows:

Step 1. Preparing a mixture with lipid molecular structure from vegetable oils, comprising the following stages:

(i) Preparing a dispersed phase of lipid molecule mixture by mixing 20 to 80 wt % of argan oil based on total oil weight, 10 to 60 wt % of olive oil based on total oil weight, and 10 to 20 wt % of camellia oil based on total oil weight, heating the mixture to a temperature between 60 and 100° C.

Argan oil, olive oil, and camellia oil are vegetable oils, which are commonly used in hair conditioners, and comprise unsaturated and saturated fatty acids as their main chemical constituents. The fatty acid with the greatest amount in argan oil and camellia oil is oleic acid, followed by linoleic acid, palmitic acid, and stearic acid (Charrouf & Guillaume, 2008; Chung, 2010; Gharby et al., 2011). Oleic acid is a monounsaturated omega-9 fatty acid that has a double bond at the 9th carbon from the methyl end of an 18-carbon chain ("Oleic Acid", 2021). Linoleic acid is a polyunsaturated omega-6 fatty acid, with two double bonds at the 6th and 9th carbons from the methyl end of an 18-carbon chain ("Linoleic Acid", 2021). Palmitic acid is a saturated fatty acid lacking double bonds in a 16-carbon chain ("Palmitic Acid", 2021). Stearic acid is a saturated fatty acid lacking double bonds in an 18-carbon chain ("Stearic Acid", 2021). Among the four fatty acids, linoleic acid and oleic acid are bulky due to double bonds and long carbon chains, while palmitic acid is the least bulky due to shorter carbon chain and the lack of double bonds. Although the main fatty acids in oils have similarities, there are differences in the composition of each fatty acid. Camellia oil contains a higher oleic acid content than argan oil, and argan oil contains a higher linoleic acid content than camellia oil. Therefore, each different mixing ratio will bring about different effects to the hair when used.

(ii) Preparing a carrier by heating propylene glycol monocaprylate (as Capryol 90), and lecithin in a propylene glycol monocaprylate:lecithin weight ratio of 5:1 to a temperature between 60 and 100° C. under vacuum rotary evaporation, followed by cooling to about 30° C. and ultrasonication for about 30 minutes; then magnetic stirring and heating at 60 to 100° C. for about 30 minutes, and then collecting the solution into the vacuum rotary evaporation system under stirring at 100° C.

When used, the lipid molecule mixture is easily denatured by light and temperature, and is often destroyed in the gastrointestinal tract. Therefore, there is a need for a process for producing microparticles containing the active oil triglyceride, having a small size, a biological coating, and a stable structure, and being non-sticky and highly soluble. Because the microemulsion system according to the invention is used in food and pharmaceutical industries, the agents selected for use must be highly safe, and have no toxicity and little side effects. Propylene glycol monocaprylate is a mixture of propylene glycol monoesters and fatty acid diesters consisting mainly of caprylic acid. The monoester and diester contents vary for the two types of propylene glycol monocaprylate (Type I and Type II), which are recognized as safe. Characterized as a specialized soluble carrier for injectable drugs, solutions (Pharmacy and Veterinary Medicine) and a viscosity adjusting and micro-emulsifying agent, it helps emulsify and form a good micro-emulsion system to increase absorption. However, if this agent is used on the skin in high doses, it will cause irritation. Therefore, to form a stable and safe microemulsion system for users, which may be used on the skin and also orally, according to the survey, the inventors combine propylene glycol monocaprylate and lecithin at a weight ratio of 5:1. Lecithin is a very popular food additive and is recognized by Europe as safe for human. Lecithin is technically a type of phospholipid, which is the component found in every cell of the human body. The chemical formulation of lecithin shows that lecithin is a fat, however, the ingredients that make up a lecithin molecule are soluble in water. This helps lecithin emulsify the vegetable oil triglycerides, allowing for dispersion in water.

(iii) Adding the carrier to the dispersed phase at a carrier: dispersed phase weight ratio of 3:1 by weight while maintaining the temperature of the carrier and dispersed phase mixture between 60 and 100° C. under stirring at 400 to 800 rpm under vacuum; then spray shooting the whole solution through a system of high pressure homogenizer with integrated dispersion nozzle.

The combination of the carrier, as a mixture of propylene glycol monocaprylate and lecithin, with specialized treatments to achieve the most optimal contact and encapsulation efficiency for the dispersed phase. By the use of a system of high pressure homogenizer with integrated dispersion nozzle to increase the encapsulation efficiency while improving the durability of the biological membrane, the oleophilic (lipophilic) ends are fully in contact and form optimal bonds. The inventors studied to produce a dispersion nozzle to integrate with the system of high pressure homogenizer, not only to employ constantly high pressure to form particles but also to allow these particles to disperse immediately after formation to avoid the phenomenon of clustered particles before being added the system expanders in the next step. This is very important to increase the stability of the nano system, increasing the performance and stability duration of the system.

(iv) Adding polysorbate 80 (such as sinopol 85 USP (Tween 80)) and polysorbate 60 (such as Tween 60) to the carrier and dispersed phase mixture obtained in step (iii) at a polysorbate 80:polysorbate 60:carrier and dispersed phase mixture weight ratio of 3:1:1 while maintaining the temperature of the carrier and dispersed phase mixture between 60 and 100° C. under stirring at 400 to 800 rpm under vacuum.

Through literature and experiments, the inventors found that to prepare nano-mixtures of lipids that are well soluble in water, the emulsion system must be in the form of an oil-in-water emulsion. The selection of emulsifiers to enhance the stability of the microemulsion system was based on the characteristics of the microemulsion system (in the form of an oil-in-water microemulsion system, a water-in-oil microemulsion system, etc.). Therefore, the inventors chose the emulsifier polysorbate (Tween) which is a combination of polysorbate 80 (Tween 80, with a hydrophilic-lipophilic balance index (HLB) of 15) and polysorbate 60 (Tween 60 (HLB: 14.5)), because polysorbate (Tween) is hydrophilic, non-toxic, and highly safe.

Because the emulsifier polysorbate (Tween) is a molecule with two separate parts, an oleophilic (lipophilic) part and an aquaphilic (hydrophilic) part, it has the ability to form bonds with the oil and the carrier mixture. The lipophilic part of polysorbate (Tween) forms bonds with vegetable oil, and the hydrophilic part of polysorbate (Tween) forms bonds with the hydrophilic part of the carrier mixture of propylene glycol monocaprylate (Capryol 90) and lecithin, thereby forming nanoparticles of lipid molecule mixture and, with this structure, well protect the activity of vegetable oil triglycerides.

(v) Cooling the resulting mixed solution to about 25° C., homogenizing the solution using an ultrasonic homogenizer, for example, with a power of 200-400 W; to achieve a size of less than 100 nm, performing ultrasonication for 30 to 60 minutes; the quality of the resulting product being controlled by dissolution in water and transparency measurement; if transparency is not met, the heating and transparency measurement is continued every 30 minutes until it is transparent, then the reaction is stopped; followed by emulsification in an emulsifying device under stirring at 400 to 800 rpm.

Nanoparticles tend to agglomerate, so for dispersion, it is necessary to provide enough energy to separate the binding forces. Using an ultrasonic homogenizer is an effective means of dispersing nanoparticles and reducing nanoparticle size, forming particles that are smaller and more uniform in size. Dispersion and disruption of nanoparticle agglomeration are the result of the actual gas invasion phenomenon caused by ultrasonic waves. When ultrasonic waves propagate into the solvent, they continuously form alternating cycles between high pressure and low pressure, which affects the binding forces of the nanoparticles. At the same time, when a series of air bubbles burst, a huge pressure will be produced on the beam of nanoparticles, causing the same to easily separate. From experiments, the inventors determined the time points for ultrasonification to produce a particle structure as needed for the product.

The process produces a lipid molecule mixture of oils such as argan oil, olive oil, and camellia oil with a particle size as adjusted for intended uses, comprising: the nanoemulsion with a particle size of 80 nm can penetrate into the cuticle and fill the whole hair follicle as well, the nanoemulsion with a particle size of 500 nm does not penetrate into the cuticle and only migrate along the hair follicle to restore and protect the outer lipid layer, and finally the nanoemulsion with a particle size of 200 nm shows a moderate across-axis distribution effect among stable nanoemulsions.

Through literature and experiments, the inventors found that to produce a lipid molecule mixture that dissolves well in water, the microemulsion system should be in the form of oil-in-water emulsion. The selection of emulsifiers to enhance the stability of the microemulsion system was based on the characteristics of the microemulsion system (in the form of an oil-in-water microemulsion system, a water-in-oil microemulsion system, etc.).

The microemulsion obtained by the process according to the invention has a pH of 7 to 7.4. With the pH value, the microparticles are stable since in such neutral environment, the bonds between lipid molecule mixture and the carrier are retained during dispersion, while when the microemulsion system has a pH<7, the bonds weaken, which leads to the destruction of nanoparticles of lipid molecule mixture in the gastrointestinal tract.

The nanoemulsion of the lipid molecule mixture obtained by the process according to the invention, which has a hydrophilic-lipophilic balance (HLB) index of 13 to 18, is a hydrophilic microemulsion system. This microemulsion system comprises microparticles containing a mixture of hydrophilic and non-aggregated lipids, with uniform particles, so it can increase water solubility, thereby enhancing the applications in a variety of products.

Step 2: Introducing lipids into chemical ingredients to form a compound for treatment of lipid loss in damaged hair as follows:

TABLE 2

| Phase | Name of cosmetic ingredient (INCI Name) | Percentage based on total ingredient weight |
|---|---|---|
| Stirring at 75° C. | Water | To 100% |
| | Disodium EDTA | 0.1 |
| | Sodium C14-16 Olefin Sulfonate | 5-7 |
| 3 | Glycerin | 2-5 |
| | glucoside Decyl | 1-5 |
| | The lipid molecule mixture obtained above | 3-5 |
| Stirring at room temperature | PEG-7 glyceryl cocoate | 0.5-1 |
| | Disodium laureth sulfosuccinate | 3-6 |
| | Cocamidopropyl betaine | 3-5 |
| | Polyquaternium-73 | 0.2-0.4 |
| | and ethylhexylglycerin Phenoxyethanol | 0.8 |
| | 25% citric acid solution | 0.2-1 |

Ingredients are weighed according to the above formulation, then a compound for treatment of lipid loss in damaged hair is produced as follows:

Dissolve disodium EDTA in water in a stirring bath.

Heat, stir at about 20 rpm, at about 75° C.

Add dissolved Sodium C14-16 Olefin Sulfonate to the stirring bath, stir for about 40 minutes at about 20 rpm, at about 75° C.

Add decyl glucoside to the stirring bath and stir at about 25 rpm, at about 75° C., with the stirring duration of about 10 minutes.

Cool the above-prepared solution to room temperature (60 minutes). During the cooling, add glycerin and PEG-7 glyceryl cocoate.

Add the mixture with lipid molecular structure to the stirring bath and stir at about 25 rpm, with the stirring duration of about 60 minutes.

Add disodium laureth sulfosuccinate to the stirring bath and stir at about 25 rpm, stop heating, with the stirring duration of about 10 minutes.

Add polyquaternium-73 to the stirring bath and stir at about 25 rpm, stop heating, with the stirring duration of about 10 minutes.

Add cocamidopropyl betaine to the stirring bath and stir at about 20 rpm, stop heating, with the stirring duration of about 10 minutes.

Add phenoxyethanol, ethylhexylglycerin, and 25% citric acid solution to the stirring bath and stir at about 20 rpm.

The homogeneity of the solution is checked via observation and centrifugation at 3000 rpm for 30 minutes. If the solution is not separated into layers and remains homogeneous, a compound for treatment of lipid loss in hair will be obtained.

According to various embodiments according to the invention, the above-mentioned lipid molecule mixture comprises the following ingredients: argan oil, olive oil, and camellia oil with the following ratio composition:

TABLE 3

| | | Argan oil | Olive oil | Camellia oil |
|---|---|---|---|---|
| Ratio | Ingredients 1 | 2 | 6 | 2 |
| | Ingredients 2 | 4 | 4 | 2 |
| | Ingredients 3 | 6 | 2 | 2 |
| | Ingredients 4 | 8 | 1 | 1 |

EXAMPLES

Example 1: Production of 200 mL of Lipid Molecule Mixture

A dispersion phase was formed by placing 10 g of a lipid molecule mixture comprising of 2 g of argan oil, 6 g of olive oil, and 2 g of camellia oil into a beaker under stirring at 400 rpm, simultaneously heated to 50° C. with an IKA magnetic hot plate stirrer with a power of 15 W.

A carrier was formed by mixing 25 g Capryol 90 (propylene glycol monocaprylate) and 5 g lecithin (5:1 ratio) and heating to 60° C. An EYELA vacuum rotary evaporation system with a power of 25 W was used, then the cooling to 30° C. was performed, followed by ultrasonification for 30 minutes. Then, it underwent magnetic stirring and heating by the IKA magnetic hot plate stirrer with a power of 15 W at 60° C. for 30 minutes, then the solution was collected into the vacuum rotary evaporation system while stirring at 100° C.

30 g of the carrier was added to 10 g of the dispersion phase prepared above, the carrier and dispersed phase mixture was further heated to 60° C. and stirred at 600 rpm, under vacuum to obtain a mixed solution of the carrier and the dispersed phase. Then the whole solution was spray shot through a system of high pressure homogenizer with integrated dispersion nozzle with a power of 200-400 W.

Sinopol 85 USP (Tween 80) and Tween 60 were added to the carrier and dispersed phase mixture obtained above at a weight ratio of 3:1:1, corresponding to 120 g of sinopol 85 USP, 40 g of Tween 60, 40 g of the carrier and dispersed phase mixture, while maintaining the temperature of the carrier and dispersed phase mixture between 60 and 100° C. under stirring at 600 rpm under vacuum, obtained 200 g of mixture.

The resulting mixture was cooled to 25° C., then an ultrasonic homogenizer with a power of 200-400 W was used to homogenize the solution. The ultrasonification duration was 30 to 60 minutes to reach a size of less than 100 nm.

The quality of the resulting product was controlled by water dissolution and transparency measurement. If transparency was not met, the heating and transparency measurement is continued every 30 minutes until it was transparent and the reaction was stopped, and the temperature was slowly lowered until it reached 50° C. At 50° C., emulsification was performed in the IKA T25 DIGITAL ULTRA-TURRAX emulsifying device with a power of 800 W at 500 rpm, for 30 minutes.

Before filling, 200 g of the nanoemulsion of lipid molecule mixture well-dispersed in water was collected.

Example 2: Production of 200 mL of Lipid Molecule Mixture

All steps and stages were performed as in Example 1, the only difference was that 10 g of the lipid molecule mixture comprised 4 g of argan oil, 4 g of olive oil, and 2 g of camellia oil.

Example 3: Production of 200 mL of Lipid Molecule Mixture

All steps, stages, and ingredients were as in Example 1, the only difference was that 10 g of the lipid molecule mixture comprised 6 g of argan oil, 2 g of olive oil, and 2 g of camellia oil.

Example 4: Production of 200 mL of Lipid Molecule Mixture

All steps and stages were performed as in Example 1, the only difference was that 10 g of the lipid molecule mixture comprised 8 g of argan oil, 1 g of olive oil, and 1 g of camellia oil.

From the four examples from Examples 1 to 4 above, four different types of oil mixtures were obtained. These mixtures would be hypothetical models for cosmetic products to evaluate the applicability of the ingredients in the formulation, so that they could be employed in production lines and real-life applications.

The UV-Vis spectroscopy method was used to quantify the content of lipid molecule mixture in the microemulsion system. The results showed that the concentrations of lipid molecule mixture in the nanoemulsion of lipid molecule mixture were 10% to 25%.

Example 5: Introduction of Lipid Molecule Mixture to Chemical Ingredients to Prepare a Compound for Treatment of Lipid Loss in Damaged Hair Ingredients were prepared as follows:

TABLE 4

| PHASE | Name of cosmetic ingredient (INCI Name) | Percentage based on total ingredient weight |
|---|---|---|
| Stirring at 75° C. | Water | 72.05 |
| | Disodium EDTA | 0.1 |
| | Sodium C14-16 Olefin Sulfonate | 7 |
| | Glycerin | 3 |
| | glucoside Decyl | 2, 5 |
| | The lipid molecule mixture obtained from Example 1 | 5 |
| Stirring at room temperature | PEG-7 Glyceryl cocoate | 0.5 |
| | Disodium laureth sulfosuccinate | 4 |

TABLE 4-continued

| PHASE | Name of cosmetic ingredient (INCI Name) | Percentage based on total ingredient weight |
|---|---|---|
| | Cocamidopropyl betaine | 4 |
| | Polyquaternium-73 | 0.25 |
| | and ethylhexylglycerin | 0.8 |
| | Phenoxyethanol | |
| | 25% citric acid solution | 0.8 |

The ingredients were weighed according to the above formulation, then sequential steps were proceeded as follows:

Disodium EDTA was dissolved in water in a stirring bath.

Heating and stirring at 20 rpm was performed at 75° C.

The dissolved Sodium C14-16 Olefin Sulfonate was added to the stirring bath under stirring for 40 minutes at 20 rpm, at 75° C.

Decyl glucoside was added to the stirring bath under stirring at 25 rpm, at 75° C., the stirring duration was 10 minutes.

The mixture was cooled to 30-32° C. (within 60 minutes). During the cooling process, glycerin and PEG-7 glyceryl cocoate were added.

The lipid molecule mixture was added to the stirring bath under stirring at 25 rpm, the heating was stopped, the stirring duration was 60 minutes.

Disodium laureth sulfosuccinate was added to the stirring bath under stirring at 25 rpm, the heating was stopped, the stirring duration was 10 minutes.

Polyquaternium-73 was added to the stirring bath under stirring at 25 rpm, the heating was stopped, the stirring duration was 10 minutes.

Cocamidopropyl betaine was added to the stirring bath under stirring at 20 rpm, the heating was stopped, the stirring duration was 10 minutes.

Phenoxyethanol, ethylhexylglycerin, and 25% citric acid solution were added to the stirring bath under stirring at 20 rpm, the heating was stopped, the stirring duration was 20 minutes.

The homogeneity of the solution was checked via observation and centrifugation at 3000 rpm for 30 minutes, if the solution was not separated into layers and remained homogeneous, a compound for treatment of lipid loss in hair would be obtained.

Example 6: Introduction of Lipid Molecule Mixture into Chemical Ingredients to Prepare a Compound for Treatment of Lipid Loss in Damaged Hair All steps, stages, and ingredients were as in Example 5, the only difference was that the lipid molecule mixture was obtained from Example 2.

Example 7: Introduction of Lipid Molecule Mixture into Chemical Ingredients to Prepare a Compound for Treatment of Lipid Loss in Damaged Hair All steps, stages, and ingredients were as in Example 5, the only difference was that the lipid molecule mixture was obtained from Example 3.

Example 8: Introduction of Lipid Molecule Mixture into Chemical Ingredients to Prepare a Compound for Treatment of Lipid Loss in Damaged Hair All steps, stages, and ingredients were as in Example 5, the only difference was that the lipid molecule mixture was obtained from Example 4.

Figure 2:
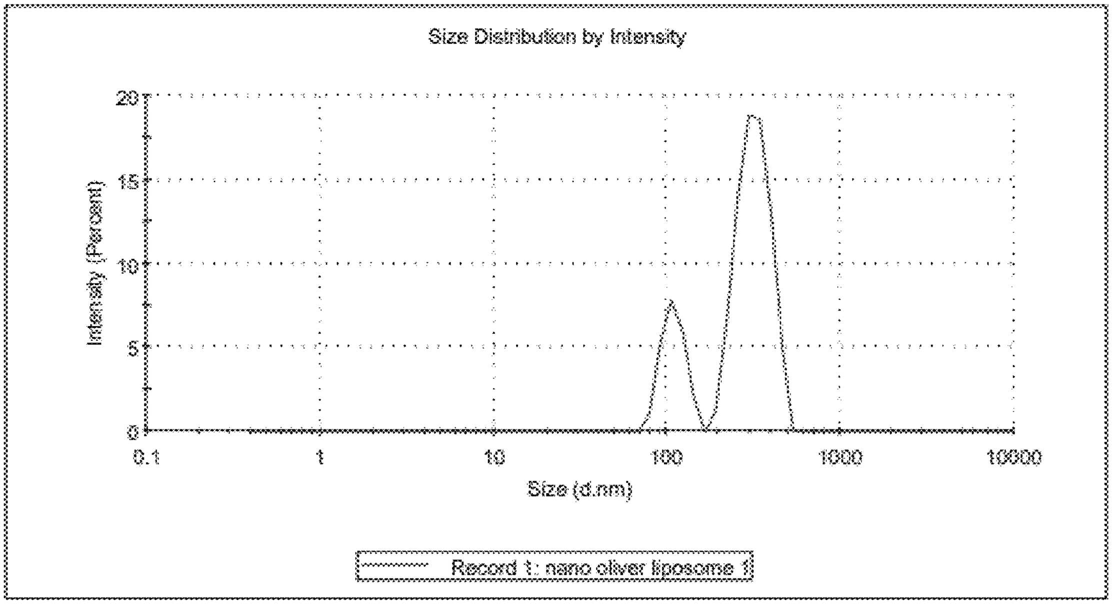
FIG. 2 shows the TEM spectrum of the nanoparticle size of the lipid molecule mixture obtained by the process according to the invention, with distribution into compatible sizes for the sites of impact on hair.
Figures 3A, 3B:
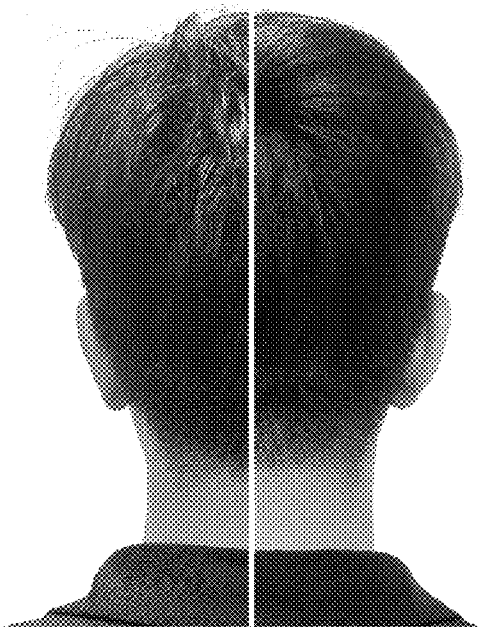
Figures 3C, 3D:
Figure 5A:
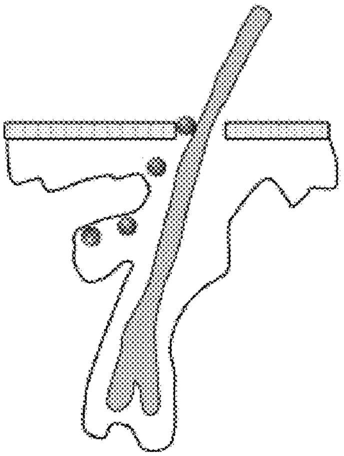
FIG. 5A illustrates a known case where nanotechnology-based particles were used to deliver therapeutic agents into hair follicles.
Figure 5B:
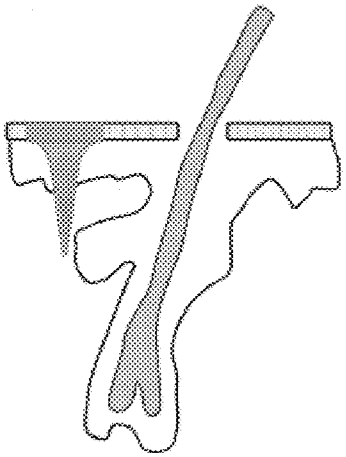
FIG. 5B illustrates a case where nanotechnology-based particles were used to deliver therapeutic agents directly to the sites surrounding hair follicles.
Figure 5C:
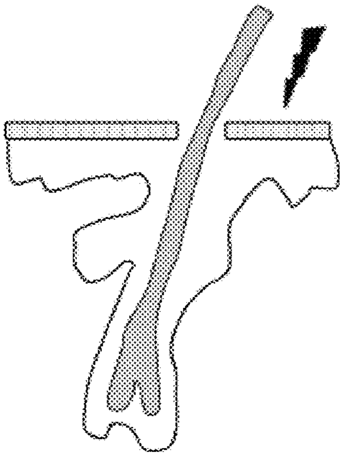
FIG. 5C illustrates a case where external stimuli lead to active release of the drug from particles with a specific release mechanism.

The size of the nanoparticles of lipid molecule mixture obtained from Examples 1 to 4 was measured using scanning TEM (Transmission electron microscopy) shown in FIG. 2, which demonstrates that the particle sizes between 20 nm and 403 nm accounted for almost a maximum of 99% in the solution. In particular:

TABLE 5

| Type of lipid molecule mixture | Nanoparticle size range (nm) |
|---|---|
| Lipid molecule mixture obtained from Example 1 | 92-403 |
| Lipid molecule mixture obtained from Example 2 | 53-205 |
| Lipid molecule mixture obtained from Example 3 | 50-101 |
| Lipid molecule mixture obtained from Example 4 | 20-53 |

Particle size measured by Dynamic Light Scattering (DLS): Particles sustained in a fluid continuously underwent random motions, and the size of the particle directly affected their speed. Smaller particles moved faster than larger ones. In DLS, lights went through samples, and scattering lights were detected and recorded at a certain angle.

TABLE 6 below shows the data measured using DLS:

TABLE 6

| The mixture obtained from Example 1 | | Diameter (nm) | Intensity % | Width (nm) |
|---|---|---|---|---|
| Average particle size (d · nm): 237.5 | Spectral peak 1 | 309.1 | 77.6 | 66.72 |
| PdI: 0.267 | Spectral peak 2 | 108.9 | 22.4 | 16.52 |
| Blocking capacity: 0.943 | Spectral peak 3 | 0.00 | 0.00 | 0.00 |
| Evaluation result: good | | | | |

Zeta potential or kinetic potential: the potential between the dispersed phase and the dispersion media of the mixtures of Examples 1, 2, 3, 4 at the same ratio.

TABLE 7

| Size (nm, according to TEM) | Size (nm, according to DLS) | Zeta potential (mV) | Stability (month) | Water solubility |
|---|---|---|---|---|
| 20-450 | 20-403 | −40 | >12 | Good water solubility, after being dissolved in water, the system stabilized >7 days |

From the above results, it is shown that the microemulsion system has small-sized microparticles (from 20 nm to 403 nm), has great stability (>12 months), good water solubility, and system stability of more than 30 days after the dissolution in water.

With reference to FIG. 1, it shows an image comparing the water dispersion between a known lipid molecule mixture and the lipid molecule mixture obtained by the process according to the invention, wherein bottle A shows the known water-dispersible lipid molecule mixture, bottle B shows the water dispersible lipid molecule mixture obtained by the process according to the invention. The lipid molecule mixture obtained by the process according to the invention was completely dispersed in water to form a transparent and homogeneous solution, while the known lipid molecule mixture was insoluble in water and floated on the surface.

With reference to FIG. 2, which is a TEM spectroscopy of the size of nanoparticles of lipid molecule mixture obtained by the process according to the invention, it is shown that the average particle size was 92 to 403 nm.

Investigation was performed on compounds for treatment of lipid loss in damaged hair obtained from Example 5 to Example 8, having the following criteria: Evaluation of hair surfaces by surface SEM imaging; Assessment of hair shine using a glossmeter; Assessment of hair softness and smoothness using a flow measuring device; Assessment of hair durability using a durability measuring device; Assessment of the lipid content that was added deeply into the hair by gravimetry.

To evaluate the effectiveness of the compound produced by the process according to the invention, the hair surface durability is evaluated by surface SEM imaging; hair shine was assessed using a glossmeter in direct comparison with silicone; hair softness and smoothness were assessed using a flow measuring device; hair durability was assessed using a durability measuring device; the lipid content that was added deeply into the hair by gravimetry was assedded. The ability of the lipid molecule mixture to protect against UV rays and reduce ROS was evaluated using an in vitro model.

The surface properties of hair strands, treated and untreated with products of the present invention before and after use were studied by SEM imaging. A shampoo containing the lipid molecule mixture showed morphological improvements in cuticle integrity (less damage) and smoothness compared to untreated hair strands.

The abilities to penetrate deeply into the hair to restore lipids, restructure the lipid layer on the hair, and analyze lipid content before and after each single use were evaluated.

In the process of preparing bleached hair samples using lipid molecule mixture, the bleached hair was wetted. Bleached hair was soaked for 15 minutes in a lipid molecule mixture solution (70 wt % lipid molecule mixture and 30 wt % of water), combined with hair strand massaging. After that, the bleached hair samples were rinsed with water, then dried, and the lipid content in the hair would be measured. Total lipid content was extracted according to the method of Bligh and Dyer. Hair sample (400 mg) was extracted with 6 mL of methanol:chloroform mixture (2:1, etc.) in a 20 mL Teflon-lined screw-cap glass tube (3 times). The samples were then heated at 50° C. for 1 h, followed by filtration to remove particulate matters using a vacuum pump through a Whatman GF/A filter (Whatman Plc, Maid-stone, UK). The residue was re-extracted twice. Chloroform (4 mL) and distilled water (4 mL) were added to the combined filtrate solution and the organic phase was separated out. After drying with $Na_2SO_4$, the solution was filtered and evaporated under reduced pressure to obtain total lipids, stored in chloroform at −5° C. The results show that the total lipid content of bleached and dyed hair after just a single use was restored to equal the amount of lipid in the original natural hair before bleaching and dyeing. Lipids were restored and penetrated deeply into the hair without being lost after rinsing.

Results from the shine, softness and smoothness, and durability tests show that the lipid molecule mixture was more effective in hair care and restoration, enhancing softness and smoothness, durability, and reducing breakage better than silicone after just a single use, and that the product produced according to the invention could completely replace silicone.

The lipid molecule mixture is a solution to reduce the amount of Reactive Oxygen Species (ROS) generated in cells when exposed to UVA light. According to the "in vitro assessment of protection from UVA light-induced oxidative stress in human keratinocytes" test of the lipid molecule mixture of the invention, it was shown that the ROS level was reduced by more than 40%. In addition, the results show that samples at the tested doses did not show any cytotoxic effects, and safety was ensured.

The surface properties of treated and untreated hair strands obtained from the process according to the invention before and after use were studied by SEM imaging. Shampoos containing lipid misture according to Examples 5 to 8 showed morphological improvements in cuticle integrity (less damage) and smoothness compared to untreated hair strands.

A basic shampoo base was used for all tests, each test being different in the conditioning agent:silicone or mixture with lipid molecular structure from vegetable oils according to the invention obtained from Examples 1 to 4. Wet and dry brushing force measurements were performed and compared. Shampoos containing the lipid molecule mixtures according to the invention (obtained from Examples 1 to 4) reduced wet brushing force by 25% and dry brushing force by 35% compared to shampoos containing only silicone. Hair shine measurements were taken before and after shampoo treatment, with heat and without heat. The combination of lipid molecule mixtures according to the invention and silicone in the shampoos resulted in a statistically significant increase ($p<0.05$) in hair shine compared to silicone with and without heat treatment. Mixture with lipid molecular structure from vegetable oils according to the invention also made hair more durable (i.e., higher tensile strength) than silicone did. The study demonstrates that the hair restoration and silicone replacement of the resulting lipid molecule mixture from the process according to the invention.

FIGS. 3A to 3D are images comparing test head halves of users, which showed shiner and smoother, more durable hair when using products obtained from the process according to the invention.

FIGS. 4A and 4B are respective images, under an electron microscope, of hair surfaces before using the compound according to the invention and after using the compound according to the invention. After using the compound according to the invention, the hair appeared smoother, the cuticle was partially restored, split ends of hair were completely sealed after a single use of the compound obtained from the process according to the invention.

The invention provides a lipid misture of argan oil, olive oil, and camellia oil, with the particle size as adjusted according to intended uses, comprising: a nanoemulsion with a particle size of 80 nm that could penetrate into the cuticle and fill the whole hair follicle as well, a nanoemulsion with a particle size of 500 nm that did not penetrate into the cuticle and only migrate along the hair follicle to restore and protect the outer lipid layer, and finally a nanoemulsion with a particle size of 200 nm that showed a moderate across-axis distribution effect among stable nanoemulsions.

The lipid molecule mixture obtained from the process according to the invention has the ability to penetrate deeply into the hair to restore lipids and restructure the lipid layer in hair. The lipid content was analyzed before and after just a single use. The results show that the total lipid content of bleached hair after just a single use was restored to equal the amount of lipids in the original natural hair before bleaching and dyeing. Lipids were restored and penetrated deeply into the hair without being lost after rinsing.

TABLE 8

| Sample name | No. | Hair sample weight (g) | Lipid weight (g) | % Lipid in hair |
|---|---|---|---|---|
| Natural black hair | 1 | 0.2278 | 0.0198 | 8.692 |
| | 2 | 0.2331 | 0.0206 | 8.837 |
| | 3 | 0.3007 | 0.0258 | 8.580 |
| Bleached hair | 1 | 0.2848 | 0.0189 | 6.636 |
| | 2 | 0.2042 | 0.0089 | 4.358 |
| | 3 | 0.4164 | 0.023 | 5.524 |
| Bleached hair after single use of the obtained oil lipid molecule mixture according to the invention | 1 | 0.2224 | 0.0199 | 8.948 |
| | 2 | 0.3124 | 0.0284 | 9.091 |
| | 3 | 0.6291 | 0.0528 | 8.393 |

The lipid molecule mixture obtained from the process according to the invention is a solution to reduce the amount of Reactive Oxygen Species (ROS) generated in cells when exposed to UVA light. According to the test "in vitro assessment of protection from UVA light-induced oxidative stress in human keratinocytes" by Wakamono company, with the purpose to evaluate the protection of nano oil/lipid molecule mixture for human HaCaT keratinocytes upon oxidative stress caused by UVA light. As a result of HaCaT cells treated with nano oil/lipid for 24 hours, the ROS level (36.9±12.7%) significantly reduced compared to untreated comparative HaCaT keratinocytes exposed to UVA light. It is shown that the antioxidant and protection from UVA was demonstrated in significantly reducing the ROS level. In addition, the results show that samples at the tested doses did not show any cytotoxic effects, and safety was ensured.

ADVANTAGEOUS EFFECTS OF THE INVENTION

The process for producing a compound for lipid treatment of hair with lipid molecule mixture and for application in cosmetic chemical according to the invention has succeeded in producing a microemulsion system with nanoparticles of lipid molecule mixture having a small particle size of 20 to 450 nm, being uniform, and having good water solubility while still retaining the structure and activity of lipid molecule mixture during nanoization.

The agents used in the process for producing lipid molecule mixtures that are well-dispersed in water are highly safe, and have no toxicity and less side effects, so the lipid molecule mixture obtained from the process according to the invention is highly safe when used.

The invention provides a lipid molecule mixture of argan oil, olive oil, and camellia oil, wherein the particle size is adjusted according to intended uses, and can penetrate deeply into the specific hair: a nanoemulsion with a particle size of 80 nm that can penetrate into the cuticle and fill the whole hair follicle as well, a nanoemulsion with a particle size of 500 nm that does not penetrate into the cuticle and only moves along the hair follicle to restore and protect the outer lipid layer, and finally a nanoemulsion with a particle size of 200 nm that shows a moderate across-axis distribution effect among stable nanoemulsions.

The application of the lipid molecule mixture obtained from the process according to the invention to the products shows the ability to penetrate deeply into the hair to restore and replenish lipids, restructure the lipid layer in hair. Analysis of the lipid content before and after using the lipid molecule mixture shows that the total lipid content in hair is doubled, the lipids penetrate deeply into the hair core, making the hair durable, soft and smooth, and reducing breakage.

The process according to the invention is simple, easy to perform, and suitable with real-life conditions in Vietnam.

What is claimed is:

1. A process for producing a compound for lipid treatment of hair using lipid molecule mixture, comprising:
- (a) preparing a mixture with lipid molecular structure from vegetable oils by:
  - (i) preparing a dispersed phase of lipid molecule mixture by mixing 20 to 80 wt % of argan oil based on total oil weight, 10 to 60 wt % of olive oil based on total oil weight, and 10 to 20% of camellia oil based on total oil weight, heating the mixture to a temperature between 60 and 100° C.;
  - (ii) preparing a carrier by heating propylene glycol monocaprylate and lecithin at a propylene glycol monocaprylate:lecithin weight ratio of 5:1 to a temperature between 60 and 100° C. under vacuum rotary evaporation, followed by cooling to about 30° C., ultrasonication for about 30 minutes, then magnetic stirring and heating at 60 to 100° C. for about 30 minutes, and then collecting the solution into the vacuum rotary evaporation system under stirring at 100° C.;
  - (iii) adding the carrier to a dispersed phase at a carrier: dispersed phase weight ratio of 3:1 while maintaining the temperature of the carrier and dispersed phase mixture between 60 and 100° C. under stirring at 400 to 800 rpm under vacuum; then spray shooting the whole solution through a system of high-pressure homogenizer with integrated dispersion nozzle;
  - (iv) adding polysorbate 80 and polysorbate 60 to the carrier and dispersed phase mixture obtained in step (iii) at a polysorbate 80:polysorbate 60:carrier and dispersed phase mixture weight ratio of 3:1:1 while maintaining the temperature of the carrier and dispersed phase mixture between 60 and 100° C. under stirring at 400 to 800 rpm under vacuum;
  - (v) cooling the resulting mixed solution to about 25° C., homogenizing the solution using an ultrasonic homogenizer, performing ultrasonication for 30 to 60 minutes to achieve a size of less than 100 nm, the quality of the resulting product controlled by dissolution in water and transparency measurement, wherein if transparency is not met, the heating and transparency measurement is continued every 30 minutes until it is transparent, then the reaction is stopped, followed by emulsification in an emulsifying device under stirring at 400 to 800 rpm;
- (b) introducing the mixture with lipid molecular structure from vegetable oils prepared above into chemical ingredients, by:
  - (i) preparing ingredients, by weight, as follows:
    - the mixture with lipid molecular structure obtained in step (a): 3-5%,
    - disodium EDTA: 0.1%,
    - Sodium C14-16 Olefin Sulfonate: 5-7%,
    - glycerin: 2-5%,
    - decyl glucoside: 1-5%, PEG-7 glyceryl cocoate: 0.5-1%,
disodium laureth sulfosuccinate: 3-6%,
cocamidopropyl betaine: 3-5%,
polyquaternium-73:0.2-0.4%
phenoxyethanol and ethylhexylglycerin: 0.8%,
25% citric acid solution: 0.2-1%,
water: to 100%;

(ii) preparing a compound for treatment of lipid loss in damaged hair, by:

dissolving disodium EDTA in water in a stirring bath;

heating under stirring at about 20 rpm at about 75° C.;

adding dissolved sodium Sodium C14-16 Olefin Sulfonate to the stirring bath under stirring for about 40 minutes at about 20 rpm, at about 75° C.;

adding decyl glucoside to the stirring bath under stirring at about 25 rpm at about 75° C., with the stirring duration being about 10 minutes;

cooling the above-prepared solution to a temperature between 30 and 32° C. for about 60 minutes; during cooling to lower the temperature, adding glycerin and PEG-7 glyceryl cocoate;

adding the mixture with lipid molecular structure to the stirring bath under stirring at about 25 rpm, stopping the heating, with the stirring duration of 60 minutes;

adding disodium laureth sulfosuccinate to the stirring bath under stirring at about 25 rpm, stopping the heating, with the stirring duration of about 10 minutes;

adding polyquaternium-73 to the stirring bath under stirring at about 25 rpm, stopping the heating, with the stirring duration of about 10 minutes;

adding cocamidopropyl betaine to the stirring bath under stirring at about 20 rpm, stopping the heating, with the stirring duration of about 10 minutes;

adding phenoxyethanol, ethylhexylglycerin, and 25% citric acid solution to the stirring bath under stirring at about 20 rpm, stopping the heating, with the stirring duration of about 20 minutes;

checking the homogeneity of the solution via observation thereof and centrifugation at 3000 rpm for 30 minutes, wherein if the solution is not separated into layers and remains homogeneous, a compound for treatment of lipid loss in damaged hair will be obtained.

2. The process for producing a compound for lipid treatment of hair using lipid molecule mixture according to claim 1, wherein in stage (i) of step (a) of the process for producing a compound for lipid treatment of hair using lipid molecule mixture, the argan oil:olive oil:camellia oil weight ratio is 2:6:2.

3. The process for producing a compound for lipid treatment of hair using lipid molecule mixture according to claim 1, wherein in stage (i) of step (a) of the process for producing a compound for lipid treatment of hair using lipid molecule mixture, the argan oil:olive oil:camellia oil weight ratio is 4:4:2.

4. The process for producing a compound for lipid treatment of hair using lipid molecule mixture according to claim 1, wherein in stage (i) of step (a) of the process for producing a compound for lipid treatment of hair using lipid molecule mixture, the argan oil:olive oil:camellia oil weight ratio is 6:2:2.

5. The process for producing a compound for lipid treatment of hair using lipid molecule mixture according to claim 1, wherein in stage (i) of step (a) of the process for producing a compound for lipid treatment of hair using lipid molecule mixture, the argan oil:olive oil:camellia oil weight ratio is 8:1:1.

* * * * *